(12) United States Patent
Sladek

(10) Patent No.: US 6,962,152 B1
(45) Date of Patent: Nov. 8, 2005

(54) RESPIRATORY EQUIPMENT SPACER ASSEMBLY

(75) Inventor: David T. Sladek, Tucson, AZ (US)

(73) Assignee: Salter Labs, Arvin, CA (US)

( * ) Notice: Subject to any disclaimer, the term of this patent is extended or adjusted under 35 U.S.C. 154(b) by 455 days.

(21) Appl. No.: 09/562,545

(22) Filed: May 2, 2000

(51) Int. Cl.⁷ ................................................. B05B 1/26
(52) U.S. Cl. .......................... 128/200.18; 128/200.19; 128/200.21; 128/200.23
(58) Field of Search ....................... 128/200.14, 200.18, 128/200.19, 200.21, 200.23, 200.24, 203.12, 204.14

(56) References Cited

U.S. PATENT DOCUMENTS

| | | | | |
|---|---|---|---|---|
| 3,301,255 A | * | 1/1967 | Thompson | 128/200.23 |
| 3,584,792 A | * | 6/1971 | Johnson | 239/424 |
| 3,767,125 A | * | 10/1973 | Gehres et al. | 239/552 |
| 4,484,577 A | * | 11/1984 | Sackner et al. | 128/203.28 |
| 4,534,343 A | * | 8/1985 | Nowacki et al. | 128/200.23 |
| D295,321 S | * | 4/1988 | Hallworth | D24/62 |
| 4,790,305 A | * | 12/1988 | Zoltan et al. | 128/200.23 |
| 4,938,210 A | * | 7/1990 | Shene | 128/203.12 |
| 4,951,661 A | * | 8/1990 | Sladek | 128/202.27 |
| 5,012,803 A | | 5/1991 | Foley et al. | |
| 5,067,655 A | * | 11/1991 | Farago et al. | 239/124 |
| 5,178,138 A | * | 1/1993 | Walstrom et al. | 128/200.23 |
| D340,975 S | * | 11/1993 | Sladek | D24/110 |
| 5,297,543 A | * | 3/1994 | Larson et al. | 128/200.23 |
| 5,301,663 A | * | 4/1994 | Small, Jr. | 128/200.18 |
| 5,474,058 A | * | 12/1995 | Lix | 128/200.18 |
| D373,630 S | * | 9/1996 | Berg et al. | D24/110 |
| 5,727,542 A | * | 3/1998 | King | 128/200.18 |
| 5,752,502 A | * | 5/1998 | King | 128/200.18 |
| 5,881,714 A | * | 3/1999 | Yokoi et al. | 128/200.14 |
| 5,881,715 A | * | 3/1999 | Shibasaki | 128/200.14 |
| 6,014,972 A | * | 1/2000 | Sladek | 128/203.12 |
| D442,685 S | * | 5/2001 | Sladek | D24/110 |

FOREIGN PATENT DOCUMENTS

| CA | 699313 | * 12/1964 | 128/200.23 |
|---|---|---|---|

* cited by examiner

*Primary Examiner*—Amanda Wieker
(74) *Attorney, Agent, or Firm*—Davis & Bujold, P.L.L.C.

(57) ABSTRACT

A spacer assembly for a ventilator or other respiratory equipment for dispensing aerosol drugs from metered dose inhaler (MDI) canisters or nebulized drugs from a nebulizer into a respiratory gas stream delivered from a ventilator or other respiratory equipment connected to a patient. The improvements involve optimizing the shape of the spacer assembly body member and providing an efficient MDI nozzle assembly to allow maximal evaporation of the propellant before the propellant droplets impact the walls of the body member while providing a compact volume for directing the output of an MDI canister or a nebulizer into the gas stream.

14 Claims, 4 Drawing Sheets

RESPIRATORY EQUIPMENT SPACER ASSEMBLY

FIELD OF THE INVENTION

The invention relates generally to respiratory apparatus and particularly to a device that can dispense a drug from a metered dose inhaler (MDI) canister into a stream of air supplied through the inspiratory path between respiratory equipment and a patient, for example, between a ventilator and an endotracheal tube in the trachea of a patient. The device is also preferably capable of introducing aerosolized medication from a nebulizer into the same air stream.

BACKGROUND OF THE INVENTION

Drugs dispensed from MDIs usually consist of very finely divided particles, typically in the 1 to 8 micron range. The medication particles are suspended in liquid propellant such as Freon or the like which is under pressure in the MDI canister. Upon actuation, a metered dose of the drug and propellant is ejected through the outlet tube of the canister and, in the prior art, out through one or at most two ports or orifices that are aimed in the longitudinal direction of the air stream to the patient. See, for example, U.S. Pat. No. 5,012,803 for a description of a single orifice nozzle and U.S. Pat. No. 5,474,058 for a two orifice nozzle construction.

As the mixture of drug and propellant is ejected out of a nozzle, it is accelerated to a high velocity so that shear forces with the nearly stationary ambient air cause the mixture to break up into many small, rapidly evaporating droplets, each of which contains hundreds to thousands of drug particles. The exit ports of the prior art dispensers typically are about 0.5 mm in diameter for single-orifice dispensers and 0.3 mm in diameter for dual-orifice dispensers.

The plume of propellant and agglomerated drug that exits a round orifice nozzle travels several tens of millimeters before the propellant can gain enough heat from the surrounding air to evaporate. The evaporation of the propellant is a phase transition that requires the input of heat to change the propellant from liquid to vapor. The rate at which heat can be transferred from the air to the propellant droplets is the limiting mechanism for their evaporation.

A major problem with MDI ventilator dispensers is that the expanding plume, consisting of unevaporated droplets containing drug particles, impinges upon the walls of the ventilator circuit and remains there, forever lost to the patient. One method to minimize this loss of drug is to add a large diameter spacer to the circuit in which the plume may expand, as described, for example, in U.S. Pat. Nos. 5,012,803; 4,484,577; 4,790,305; 4,938,210 and 5,178,138.

There are, however, several disadvantages associated with use of large-volume spacers. Their weight tends to pull on the ventilator tubing which is inserted into the patient's trachea which may cause the patient considerable physical discomfort. They also collect contaminated fluid. The volume of the spacer is also a hindrance to optimal air flow to the patient because the spacer adds needless volume to the circuit. And, in collapsible versions of a large-volume spacer, such as described in U.S. Pat. No. 4,938,210 the spacer may be difficult to open once it has been collapsed.

An advantage exists, therefore, for an aerosolized medication delivery device that would enable rapid expansion and evaporation of the medication's pressurized propellant, thereby resulting in a compact, lightweight device which would efficiently deliver medication yet not cause the patient undue discomfort.

SUMMARY OF THE INVENTION

It is an object of this invention to provide an improved delivery of drug from an MDI to an intubated patient. It is a further object of this invention to provide a spacer of smaller volume to reduce the compressibility effects. It is a further object to provide a spacer of smaller weight to reduce the load applied to the tubing attached to the patient. It is a further object to provide a spacer that efficiently uses all of its internal volume to evaporate more of the propellant before it can impact the walls of the spacer and inhibit drug delivery to the patient. It is a further object to provide a novel nozzle that minimizes the distance that the plume will travel before the propellant is evaporated. It is a further object of this invention to provide a device that can be used for both MDI delivery and the delivery of aerosolized medication from a nebulizer. The present invention provides a spacer assembly suitable for disposition into the respiratory gas stream of a patient, especially an intubated patient attached to a ventilator. The spacer assembly is preferably capable of dispensing mists of aerosolized drugs from an MDI canister as well as nebulized medications from a small volume nebulizer. The spacer assembly preferably comprises a body including an expansion chamber having an inlet and an outlet adapted for connecting the spacer assembly to the air flow tubing of a conventional ventilator or other respiratory equipment operable to deliver a pressurized flow of therapeutic respiratory gas.

The expansion chamber preferably includes a first opening for receiving an MDI nozzle assembly and a second opening for receiving a discharge outlet of a conventional nebulizer or the like. The second opening is preferably sealed by a spring-biased valve or the like when the spacer body is disconnected from a nebulizer. According to a preferred embodiment, the MDI nozzle assembly includes multiple, radially arranged channels terminating in outlet ports which collectively function to dispense liquid propellant-borne medication in a diffuse, gentle, generally umbrella shaped mist or plume of finely atomized drops which allows the propellant to rapidly evaporate upon discharge into the expansion chamber. In so doing, the volume of the expansion chamber and, thus, the outer dimensions and weight of the spacer assembly body may be reduced. By virtue of the compact size of the spacer assembly body, the medication is more efficaciously delivered to the patient. More specifically, less medication is wasted by virtue of impingement of unevaporated medication laden droplets on the interior walls of the spacer body. And, surplus compressible volume is eliminated from the breathing circuit.

The combined benefits realized by the cooperating structural features of the spacer assembly include, without limitation, superior performance and enhanced patient comfort in a lightweight compact device which may be readily connected to the ventilator tubing or the breathing circuit of any suitable therapeutic respiratory equipment heretofore known in the art.

Other details, objects and advantages of the present invention will become apparent as the following description of the presently preferred embodiments and presently preferred methods of practicing the invention proceeds.

BRIEF DESCRIPTION OF THE DRAWINGS

The invention will become more readily apparent from the following description of preferred embodiments thereof shown, by way of example only, in the accompanying drawings, wherein:

Figure 1:
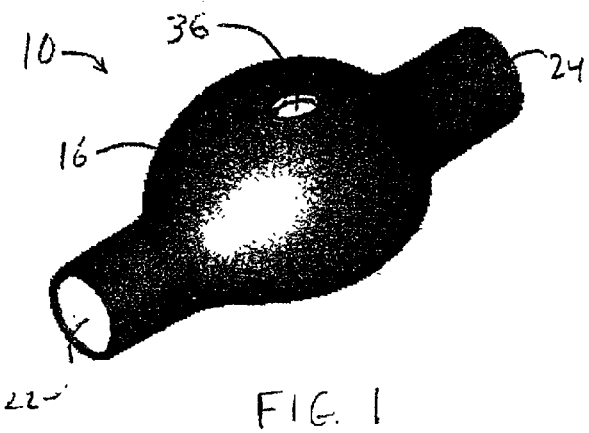
FIG. 1 is a perspective view of a body member of a ventilator spacer assembly in accordance with the present invention.
Figure 2:
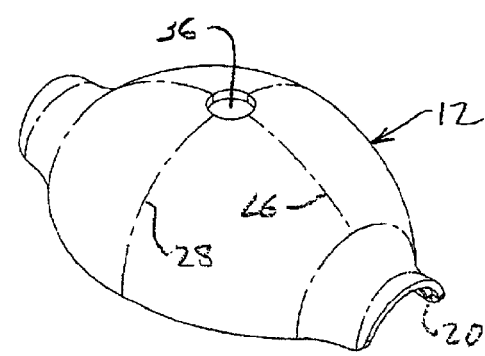
FIG. 2 is a perspective view of a first portion of the body member of FIG. 1.
Figure 3:
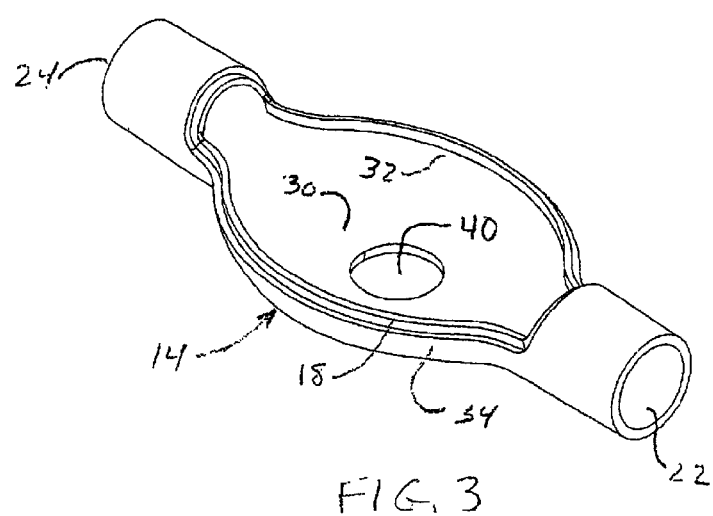
FIG. 3 is a perspective view of a second portion of the body member of FIG. 1.
Figure 4:
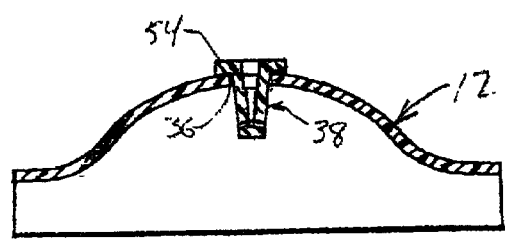
FIG. 4 is an elevational cross-section view of a n MDI nozzle assembly according to the present invention shown disposed in the body member first portion shown in FIG. 2.
Figure 5A:
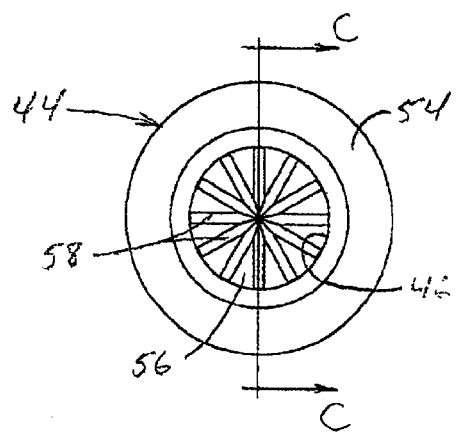
FIG. 5A is a top plan view of a first component of an MDI nozzle assembly according to the present invention.
Figure 5B:
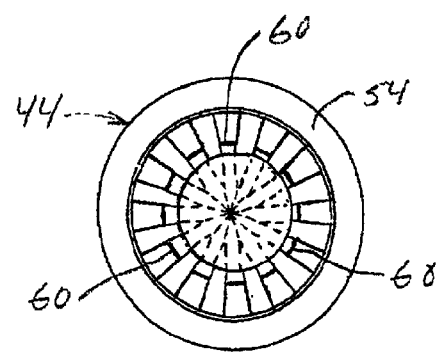
FIG. 5B is a bottom plan view of the first MDI nozzle assembly component shown in FIG. 5A.
Figure 5C:
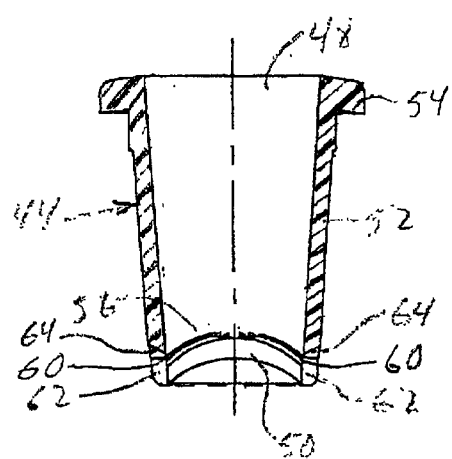
FIG. 5C is an elevational cross-section view of a first component of an MDI nozzle assembly according to the present invention taken along line C—C of FIG. 5A.

FIG. 8 is a top plan view of a valve according to the present invention that is suitable for attachment to the second body portion of FIG. 3 and operable to selectively seal the interior of the spacer assembly body member and receive the discharge outlet of a conventional nebulizer; and FIG. 9 is an elevational cross-section view of the valve of FIG. 8 shown disposed interiorly of the body member first portion shown in FIG. 3 and operatively displaced by the discharge outlet of a conventional nebulizer.

DETAILED DESCRIPTION OF THE INVENTION

Referring to FIGS. 1–4 collectively, there is shown a presently preferred construction of a ventilator spacer body number 10 (FIG. 1), including a first portion 12 thereof (FIG. 2) and a second portion 14 thereof (FIG. 3), of the ventilator spacer assembly of the present invention. When assembled, the body member 10 defines a bulbous yet compact medicament expansion chamber. Preferably, the central region 16 of body member 10 is at least semi-spheroidal with the first portion 12 defining an outwardly bulging profile and the second portion 14 defining a predominantly flat profile, whereby central region 16 assumes a generally turtle shell shape. First and second portions 12, 14 of body member 10 may be fabricated from any suitable rigid to substantially rigid metallic or plastic material. Presently preferred materials include ABS, polycarbonate or the like. To facilitate alignment and assembly of the first and second portions 12, 14 one of the first and second body portions is desirably provided with a preferably continuous ridge which is received in a corresponding recess in the other body portion in a tongue-and-groove connection. As shown in FIG. 3 such ridge is identified by reference numeral 18, and, in FIG. 2, the mating recess is represented by reference numeral 20. Upon respective attachment to an MDI nozzle assembly and nebulizer valve assembly described in greater detail in connection with the remaining figures, first and second portions 12, 14 of body member 10 are preferably fixedly attached to one another by welding, heat bonding, solvent bonding or adhesive bonding or other conventional means or methods that may be appropriate for the materials of fabrication of the first and second portions.

Body member 10 has an inlet 22 and outlet 24 of a size suitable for friction connection to conventional ventilator or other respiratory equipment flexible supply tubing (not shown). Preferably, a horizontal plane through the centers of the inlet 22 and outlet 24 establishes a datum plane between the first and second body members 12, 14.

The first body portion 12 is substantially one-half of an ellipsoid or similar spheroid bisected by the datum plane. Body member 10 is preferably nearly symmetrical to symmetrical about a first vertical plane (dot-dash line 26, FIG. 2) passing through the centers of inlet 22 and outlet 24. Similarly, body member 10 is preferably nearly symmetrical to symmetrical about a second vertical plane (dot-dash line 28, FIG. 2) extending perpendicular to first vertical plane 26 and disposed at the midpoint of the longitudinal dimension of the body member.

The second body portion 14 is preferably generally tray-shaped and includes a flat, substantially oval bottom 30 with upwardly turned side walls 32 and 34 which mate with first body portion 12, preferably at the datum plane. All interior and exterior surfaces of the body member 10 are desirably gently blended and rounded to minimize bulk and weight and to promote efficient respiratory gas flow through the body member.

The first body portion 12 includes a first aperture 36 for receiving an MDI nozzle assembly 38 as shown in FIGS. 4 and 7. The second body portion 14 also preferably includes a second aperture 40 for cooperating with a valve assembly 42 as shown in FIGS. 8 and 9. FIGS. 5A–5C provide several views of a first component 44 of MDI nozzle assembly 38 constructed according to the present invention. Like body member 10, the MDI nozzle assembly 38, including first component 44 and second component 46 (FIG. 6), may be fabricated from any suitable substantially rigid to rigid metal or plastic such as ABS, polycarbonate or the like. First component 44 is a generally cylindrical, receptacle-like member having an open top 48, a closed bottom 50 and a continuous circumferential wall 52 contiguous with bottom 50. Circumferential wall 52 is preferably slightly tapered to enable the first nozzle component 44 to snugly receive the correspondingly shaped second MDI nozzle component 46 in the manner shown in FIG. 6. The upper end of circumferential wall 52 is preferably bounded by a radially outwardly directed annular flange 54 for enabling the MDI nozzle assembly 38 to reside within the first aperture 36 of the first body portion 12 as shown in FIGS. 4 and 7. Once seated in the first aperture 36, the MDI nozzle assembly 38 may be welded or bonded to the first body portion 12 at flange 54 to affix assembly 38 to first body portion 12.

The MDI nozzle assembly 38 includes means for discharging a generally annular or, more preferably, generally umbrella shaped plume of medicine-containing propellant. According to a presently preferred construction, the bottom 50 of first nozzle component 44 defines a convex inner surface 56 in which are preferably provided, such as by forming or cutting, a plurality of radial channels 58. These channels, which are preferably equiangularly arranged and number at least three and preferably at least six or more, may be envisioned as meridians emanating from the north pole of a sphere. Most preferably, channels 58 comprise twelve equiangularly spaced grooves of generally semicircular or U-shaped cross-section. However, it is contemplated that more or less than twelve channels 58 may be provided in the inner surface 56 of the enclosed bottom 50 of the first nozzle component 44 and that such channels may have cross-sectional configurations other than generally semicircular or U-shaped. Each channel 58 terminates at a small port 60 of about 0.10 to about 0.30 mm in size provided in circumferential wall 52. Additionally, the circumferential wall 52 is preferably somewhat beveled, as indicated by reference numeral 64, at the mouths of ports 60 to allow the plume of medicine containing propellant to expand without obstruction upon exiting the ports. In the absence of bevels 64, unevaporated droplets might collect at the mouths of ports 60 thereby wasting medicine and hindering flow of the propellant.

Figure 6:
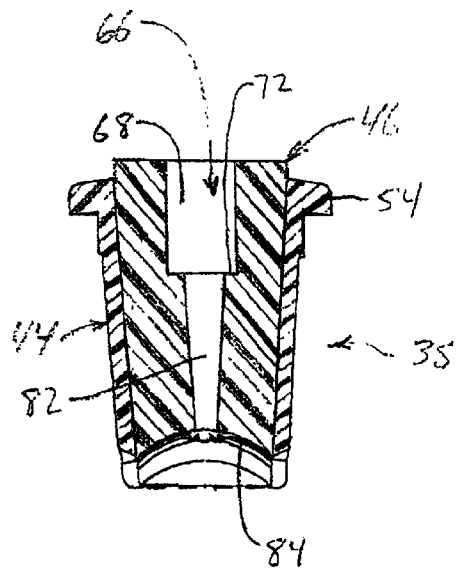
FIG. 6 is an elevational cross-section view of an assembled MDI nozzle assembly according to the present invention.

Referring to FIG. 6, there is shown a fully assembled MDI nozzle assembly 38 constructed in accordance with the present invention. As illustrated, second nozzle component 46 is preferably of a size and shape to be snugly received within the first component 44. The first and second components 44, 46 may be permanently affixed to one another by any suitable bonding means or methods known in the art. Second component 46 includes a central passageway 66 comprising a first portion 68 defining a shoulder 72 against which the discharge stem 76 (FIG. 7) of a conventional MDI canister 80 abuts during operation of the ventilator spacer assembly in an MDI mode of operation. It will be appreciated that the shape and size of stepped portion 68 may be varied to accommodate the discharge stems of any sort of MDI canister.

Beneath the stepped portion 68, central passageway 66 further includes a product delivery portion 82 through which a pressurized flow of medication-containing droplets is conveyed when MDI canister 80 is depressed to activate its internal outlet valve. Product delivery portion 82 of central passageway 66 terminates at a bottom surface 84 of second component 46. Bottom surface 84 is preferably concave and has a radius of curvature corresponding to or, more preferably, substantially the same as the radius of curvature of convex inner surface 56 of the bottom 50 of first nozzle component 44. The first and second nozzle components 44, 46 are dimensioned such that, when the second component is received in the first, the convex inner face 56 of the first component 44 contacts the concave bottom surface 84 of the second component 46.

Figure 7:
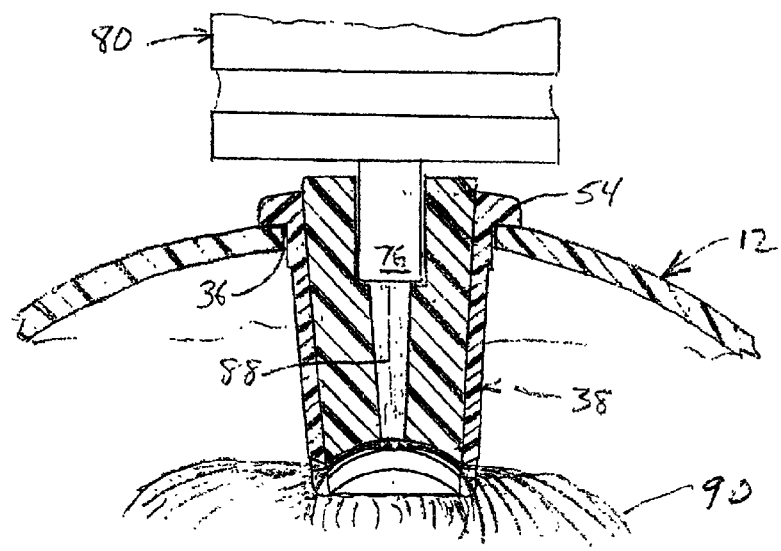
FIG. 7 is an elevational cross-section view of an MDI nozzle assembly according to the present invention shown disposed in the body member first portion shown in FIG. 2 and dispensing a plume of aerosolized medication.
Figure 8:
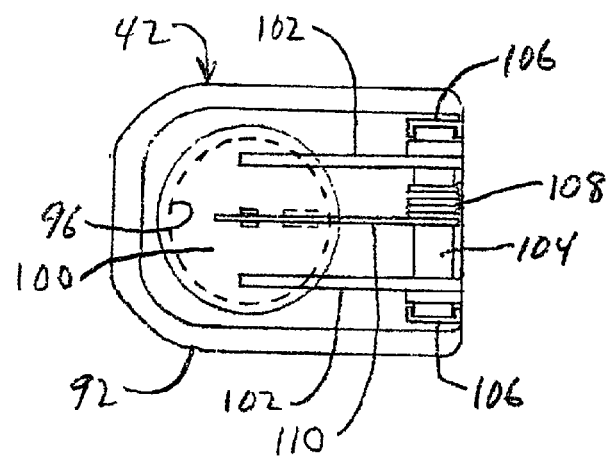

FIG. 7 shows the MDI canister 80 in a depressed or activated state wherein it is discharging a stream 88 of medicine-containing liquid into the product delivery portion 82 of the central passageway 66. Upon exiting product delivery portion 82, the product stream 88 impinges upon the radially innermost regions of channels 58. Thereafter, the flow radiates outwardly through the channels 58 and is discharged through ports 60 as a diffuse gentle mist or plume 90.

According to a presently preferred construction, the MDI nozzle assembly 38 preferably includes twelve ports 60 which, by virtue of the curvature of channels 58, cause plume 90 to assume a general umbrella shape upon discharge from the assembly thus enabling the propellant to rapidly evaporate. As such, the medicine is quickly entrained in the respiratory flow circuit and delivered to the patient. The dispersion and rapid evaporation of the propellant in the plume 90 allows the spacer assembly body member 10 to have a small expansion chamber volume. This coupled with the fact that in a preferred construction the plume 90 is generally umbrella shaped enables the interior space of the body member 10 to be even further reduced and, preferably, mimic the shape of the plume. Reduced interior volume, in a preferred embodiment about 110 cc, translates to reduced exterior dimensions and weight. A ventilator spacer assembly body member of such size and weight, in turn, more effectively conveys medicine to the patient while avoiding much of the patient discomfort associated with the relatively bulky and heavy ventilator spacers heretofore known in the art.

By way of comparison, the surface area of a typical 0.5 mm diameter orifice or nozzle discharge port as used in the prior art, is approximately 2.5 $mm^2$, whereas the sum of the surface areas of the channels 58 in the preferred twelve channel embodiment of MDI nozzle assembly 38 is approximately 23 $mm^2$. This is an increase of approximately 900% in wetted area for the present nozzle assembly versus circular single or double port prior art nozzles. The large increase in wetted area adds significant friction to the flow of propellant/drug mixture, slowing its velocity while simultaneously producing great turbulence and shear to cause the exiting mixture to atomize into small droplets. The velocity of the emerging plume 90 is considerably reduced when compared to the exit velocity from one or two round unitary nozzles of the same area. The reduced velocity allows the walls of the body member 10 to be closer to ports 60 without the droplets impacting the walls. The radially emerging plume 90 impinges upon significantly more air as it exits the multiple ports 60 than does a prior art plume. More particularly, plume 90 has much more surface area for mixing with the surrounding air since its geometry is generally umbrella-shaped and inclined downwardly at approximately 300 from horizontal whereby surrounding air contacts both the top and bottom sides of the radially expanding plume. In contrast, a prior art plume that exits a circular orifice is a solid cone with an included angle of about 60° which presents rather limited volume available for contact by the surrounding air. In the current invention, the droplets of propellant in the expanding plume 90 are surrounded by considerably more air and thus heat can be transferred from the air to the propellant droplets more quickly. Hence, the propellant droplets can evaporate more quickly than in plumes generated by prior art spacer devices. The air within a spacer expansion chamber is essentially at rest when compared to the velocity of an expanding plume. Since the umbrella-shaped plume 90 of the present invention has much more volume contacting the air within the expansion chamber, it evaporates faster than prior art plumes. Consequently, accelerated evaporation allows the inner walls of the body member 10 to be closer to the ports 60 in comparison with prior spacer devices. This, in turn, allows the size of the spacer body member 10 of the present invention to be smaller than prior devices, while simultaneously minimizing the amount of drug that is deposited on the inner surfaces of the body member.

Although according to a presently preferred embodiment the plume discharging means of MDI nozzle assembly 38 is constructed as a plurality of radially disposed channels 58, it is contemplated that other means capable of producing the desired plume configuration may be used. For example, rather than at least three channels 58 of substantially uniform cross-sectional area, such means alternatively may be constructed as one or more passageways of radially increasing cross-sectional area suitable for discharging a generally annular and, more preferably, generally umbrella shaped medicament containing plume 90.

FIGS. 8 and 9 reveal a further aspect of the present invention. According to a presently preferred construction, second portion 14 of body member 10 includes the aforementioned aperture for cooperating with a valve 42. Valve 42, which is preferably constructed as a gate valve, includes a base 92 that may be adhered or otherwise fastened to the inside face of bottom 30 of second body portion 14. Integral with and upwardly extending from base 92 is a cylindrical throat 94 having an opening 96 for closely receiving a discharge outlet 98 of a conventional nebulizer (not shown).

Figure 9:
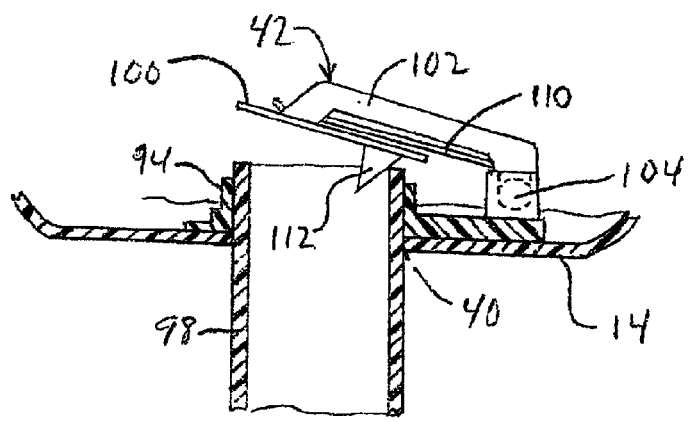

When disconnected from a nebulizer, valve 42 seals opening 96 from the ambient atmosphere. More particularly, valve 42 further comprises a gate 100 of larger diameter than opening 96 which is connected by one or more, arms 102 to a pivot shaft 104 that, in turn, is rotatably supported in upstanding brackets 106. Gate 100 is normally biased to a closed position by a torsion spring 108 having a first leg (not illustrated) in contact with the base 92 and a second leg 110 in contact with gate 100. Preferably, gate 100 further comprises a downwardly depending cam member 112 to promote smooth opening and closing of the gate as the nebulizer discharge outlet 98 is inserted into and withdrawn from body member 10. When the nebulizer discharge outlet is inserted through aperture 40 and opening 96, it comes into contact with cam member 112. Further insertion of nebulizer discharge outlet 98 urges gate 100 from seating contact with throat 94 to the position shown in FIG. 9. When the nebulizer discharge outlet 98 and gate 100 are so disposed, the patient may inhale the pressurized, medicine-containing air delivered by the nebulizer for as long as desired or necessary. When the therapy is completed, the nebulizer discharge outlet is withdrawn from throat 94 and aperture 40 and gate 100 returns to its seated position against the top of throat 94. The presence of such nebulizer accommodation structure thus renders the ventilator spacer assembly of the present invention a dual-utility device selectively adaptable to both MDI and nebulizer medication dispensing applications.

Although the invention has been described in detail for the purpose of illustration, it is to be understood that such detail is solely for the purpose and that variations can be made therein by those skilled in the art without departing from the spirit and scope of the invention except as it may be limited by the claims.

What is claimed is:

1. A spacer assembly for attachment to a breathing circuit of respiratory equipment, said spacer assembly comprising:
    a hollow body member defining a medicament expansion chamber, said body member having an inlet and an outlet contiguous with said expansion chamber that are dimensioned for attachment to the breathing circuit;
    a first aperture in said expansion chamber for cooperating with a metered dose inhaler; and
    a second aperture in said expansion chamber for cooperating with a nebulizer.

2. The spacer assembly of claim 1 further comprising a metered dose inhaler nozzle assembly operably connected to said first aperture.

3. The spacer assembly of claim 1 further comprising valve means operably connected to said second aperture for enabling selective insertion and withdrawal of a nebulizer discharge outlet into and out of said body member, said valve means including means for sealing the interior of said body member from the ambient atmosphere when a nebulizer discharge outlet is not inserted into said body member.

4. In a metered dose inhaler nozzle assembly adapted for use with a spacer assembly connectable to a breathing circuit of respiratory equipment, the improvement comprising port means arranged around said nozzle assembly for discharging a generally annular plume of medicine containing propellant around said nozzle assembly.

5. The nozzle assembly of claim 4 wherein said plume is generally umbrella shaped.

6. A metered dose inhaler nozzle assembly adapted for use with a spacer assembly connectable to a breathing circuit of respiratory equipment, said nozzle assembly comprising:
    a circumferential wall;
    a bottom contiguous with said wall;
    at least three ports in said wall arranged around said nozzle assembly for discharging a generally annular plume of medicine containing propellant around said nozzle assembly; and
    a passageway having at least one shoulder adapted for abutting contact by a discharge stem of a metered dose inhaler canister, said passageway including a product delivery portion in communication with said at least three ports.

7. The nozzle assembly of claim 6 including at least three channels in communication with said product delivery portion and terminating at said at least three ports.

8. The nozzle assembly of claim 6 wherein said channels are curved.

9. The nozzle assembly of claim 6 wherein said wall includes a radially outwardly directed flange for enabling said nozzle assembly to reside within a body member of a spacer assembly.

10. The nozzle assembly of claim 6 wherein said nozzle assembly comprises:
    a first component having an open top and including said circumferential wall, said bottom and said at least three ports, said bottom having an inner face; and
    a second component dimensioned for insertion into said first component, said second component including said passageway, said second component further including a bottom surface.

11. The nozzle assembly of claim 10 wherein bottom surface is concave and said inner surface is convex.

12. The nozzle assembly of claim 11 wherein said inner surface includes at least three radial channels each respectively terminating at one of said at least three ports.

13. The nozzle assembly of claim 10 wherein said bottom surface is adapted for contacting said inner face.

14. A spacer assembly for attachment to a breathing circuit of respiratory equipment, said spacer assembly comprising:
    a hollow body member having an inlet and an outlet dimensioned for attachment to the breathing circuit;
    an aperture in said body member for cooperating with a metered dose inhaler; and
    a metered dose inhaler nozzle assembly operably connected to said aperture, said nozzle assembly comprising:
        a circumferential wall;
        a bottom contiguous with said wall;
        at least three ports in said wall arranged around said nozzle assembly for discharging a generally annular plume of medicine containing propellant around said nozzle assembly; and
        a passageway having at least one shoulder adapted for abutting contact by a discharge stem of a metered dose inhaler canister, said passageway including a product delivery portion in communication with said at least three ports.

\* \* \* \* \*